US005574189A

United States Patent [19]

Vedage et al.

[11] Patent Number: 5,574,189
[45] Date of Patent: Nov. 12, 1996

[54] HYDROGENATION OF NITRILES TO PRODUCE AMINES

[75] Inventors: Gamini A. Vedage, Bethlehem; John N. Armor, Orefield, both of Pa.

[73] Assignee: Air Products and Chemicals, Inc., Allentown, Pa.

[21] Appl. No.: 382,739

[22] Filed: Feb. 2, 1995

[51] Int. Cl.⁶ ................................................. C07C 209/48
[52] U.S. Cl. ........................... 564/493; 564/415; 564/490
[58] Field of Search ..................................... 564/415, 493

[56] References Cited

U.S. PATENT DOCUMENTS

| | | | |
|---|---|---|---|
| 2,165,515 | 7/1939 | Schmidt | 260/583 |
| 2,781,399 | 2/1957 | Shapiro | 260/583 |
| 3,177,258 | 4/1965 | Rylander et al. | 260/611 |
| 3,673,251 | 6/1972 | Frampton et al. | 260/563 D |
| 4,739,120 | 4/1988 | Zuckerman | 564/385 |
| 5,047,178 | 9/1991 | Ganguli et al. | 260/409 |
| 5,075,506 | 12/1991 | Zimmerman | 564/490 |
| 5,130,491 | 7/1992 | Zimmerman | 564/490 |
| 5,235,108 | 8/1993 | Borininhof et al. | 564/490 |
| 5,254,737 | 10/1993 | Zimmerman | 564/490 |

FOREIGN PATENT DOCUMENTS 4947304  11/1972  Japan.

OTHER PUBLICATIONS

Volf, Jiri and Josef Posek "Hydrogenation of Nitriles" Studies in Surface Science & Catalysis, vol. 27 pp. 105–144 1986.

*Primary Examiner*—Brian Burn
*Attorney, Agent, or Firm*—Mary E. Bongiorno; Russell L. Brewer

[57] ABSTRACT

This invention relates to an improvement in a process for the production of amines and particularly secondary amines by the hydrogenation of aliphatic and aromatic nitriles. The improvement resides in the use of a multi-metallic catalyst, preferably a bimetallic catalyst comprising nickel or cobalt in combination with rhodium, ruthenium or palladium. Optionally, the catalyst is carried on an alumina support.

14 Claims, No Drawings

HYDROGENATION OF NITRILES TO PRODUCE AMINES

FIELD OF THE INVENTION

This invention relates to a hydrogenation process for the production of amines by the hydrogenation of aliphatic and aromatic nitriles.

BACKGROUND OF THE INVENTION

Catalytic processes for the hydrogenation of aliphatic and aromatic nitriles to produce amines are known. Representative patents illustrating the hydrogenation of nitriles to produce various amines are as follows:

U.S. Pat. No. 5,130,491 discloses a method for the production of secondary amines from fatty nitriles, e.g., tallow nitrile, utilizing a nickel catalyst promoted with copper, chromium or molybdenum. Secondary amine production is enhanced by hydrogenating the nitrile in a two-stage process with the second stage being carried out in the absence of ammonia. Temperatures range from 100°–200° C. while pressures range from 50–5000 psig.

U.S. Pat. No. 2,781,399 discloses a process for producing long-chain dialiphatic secondary amines as well as dialkyl and dialkylene amines and aromatic secondary amines and aromatic aliphatic secondary amines. The patent notes that the reaction to produce secondary amines is difficult to control and yet obtain a desired secondary amine product of good color and quality at acceptable reaction rates. The catalytic hydrogenation of the aliphatic nitrile is carried out using a nickel catalyst, preferably Raney nickel under anhydrous conditions. Alkali and alkaline earth metal hydroxide addition is undesirable when the feed source contains small amounts of free fatty acids.

U.S. Pat. No. 4,739,120 discloses a process for the hydrogenation of nitriles to primary amine using a rhodium catalyst. The reaction is carried out in the presence of a two phase solvent system comprising an aqueous phase and an immiscible organic phase.

U.S. Pat. No. 5,235,108 discloses a process for preparing secondary alkyl amines by the hydrogenation of alkyl nitriles using a nickel-containing catalyst-containing copper as a promoter. The patent suggests catalytic systems for the hydrogenation of nitriles which include catalyst components of nickel, copper and cobalt as well as dual systems, e.g., nickel-copper chromite and cobalt-copper chromite.

U.S. Pat. No. 3,177,258 discloses a process for the hydrogenation of unsaturated materials, such as unsaturated hydrocarbons and aliphatic and aromatic nitriles. The catalyst used for effecting hydrogenation is a ruthenium-containing catalyst combined with a platinum metal, e.g., ruthenium combined with platinum, palladium or rhodium. In the hydrogenation of propionitrile, coprecipitated and mixed metal ruthenium-platinum and ruthenium-palladium complexes gave high concentrations substantial levels of tertiary amine while the ruthenium-rhodium catalyst composition give high concentrations of secondary amines.

U.S. Pat. No. 3,673,251 discloses a cyclic process for producing mono, secondary and tertiary polyamines by continuously hydrogenating the nitrile in the presence of a hydrogenation catalyst such as cobalt, platinum, palladium, nickel and so forth.

U.S. Pat. No. 5,075,506 discloses ;a process for producing secondary amines by the hydrogenation of nitriles over a cobalt catalyst promoted with zirconium.

U.S. Pat. No. 2,165,515 discloses a process for the production of amines by the catalytic hydrogenation of nitriles using cobalt and cobalt promote with barium or manganese.

An article, *Hydrogenation of Nitriles*, J. Volf and J. Posek; Studies in Surface Science & Catalysis, Volume 27, p.105–144, 1986 discloses the hydrogenation of nitriles using a variety of catalysts, e.g., nickel, cobalt, rhodium, ruthenium, platinum and palladium. The effect of these catalysts on product slate is also shown.

SUMMARY OF THE INVENTION

This invention relates to an improvement in a process for the production of amines including secondary amines by the hydrogenation of aliphatic and aromatic nitriles. The improvement resides in the use of a multi-metallic catalyst, preferably a bimetallic catalyst comprising nickel or cobalt in combination with rhodium, ruthenium or palladium. Optionally, the catalyst is carried on an alumina support.

There are significant advantages associated with the utilization of the catalyst described herein for generating secondary amines. They include:

- an ability to hydrogenate nitriles and generate primary amines in high selectivity;
- an ability to hydrogenate nitriles and generate a product slate containing secondary aliphatic amines in relatively large amounts;
- an ability to reduce catalyst levels required for hydrogenation of nitriles in amine formation due to the high activity of the catalyst system; and,
- an ability to operate over an extended period of time without catalyst regeneration.

DETAILED DESCRIPTION OF THE INVENTION

The catalytic process for the hydrogenation of aliphatic and aromatic nitriles using the catalysts described herein is carried out using procedures commonly used in the art. Catalytic hydrogenation of a variety of nitriles can be performed by the described process. These nitriles include aliphatic mononitriles, preferably those having from 2–10 carbon atoms, and aliphatic dinitriles preferably having from 4–10 carbon atoms. Exemplary nitriles include acetonitrile, propionitrile, butyronitrile, valeronitrile, capronitrile, 2,2-dimethylpropanenitrile, glutaronitrile, adiponitrile, malononitrile, 1,3,5-tricyanopentane, and bis-cyanoethyl ether. Cycloaliphatic nitriles include cyclobutanecarbonitrile, cyclopentanecarbonitrile and so forth. The process is also adapted for the hydrogenation of aromatic nitriles, and representative aromatic nitriles include benzonitrile, p-tolunitrile, aminobenzonitrile, phenylacetonitrile, naphthylnitrile and so forth.

The catalyst used in effecting hydrogenation of the nitrile is one containing cobalt or nickel in combination with rhodium, ruthenium, platinum, or palladium. The metal combination is preferably carried on a support conventionally used for these types of processes, such supports being alumina, carbon, kieselguhr, silica, silica-alomina, bentonite, titania, zirconium oxide, and the like. Although the supports are generally inert, they may be somewhat active so long as they do not adversely interfere with the hydrogenation process. For reasons of efficiency and economy the preferred support is alumina and the metals are carried upon the same support.

The cobalt or nickel metal component of the catalyst, including the support, generally is present in an amount from about 1 to 60% by weight and preferably from about 5 to 25% by weight. The other metallic component(s), e.g., rhodium, ruthenium,, or palladium, is present in a manner from 0.01 to about 10% by weight, preferably from about 0.5 to 2% by weight of the catalyst including support. Other metallic catalyst components may be added, if desired. The metal components of the catalyst can be present as a bimetallic catalyst, i.e., at least two of the described metals are present on the same support, or the catalyst may be present as a physical admixture. Typically, the bimetallic catalysts are formed by the coprecipitation of at least two metals on a single support. A physical mixture is distinguished from a bimetallic catalyst in that in the physical mixture each metal component is carried on a separate support, e.g., each is carried on a separate alumina support. The resulting catalyst then is blended together in appropriate ratios to provide the desired cobalt or nickel to metal ratio.

The catalyst levels used in effecting hydrogenation of the nitrile component are those commonly used in conventional hydrogenation processes of this type. Broadly, the catalyst loading, as a percent of the nitrile component, to be hydrogenated is from about 0.1 to about 10% by weight. Conventional levels are more commonly within a range from about 1 to 5% by weight. The level of catalyst employed is one that can be appropriately selected by the practitioner.

Conditions effective for hydrogenating the aliphatic and aromatic nitriles are those conventionally used in the prior art. However, this process is highly effective at relatively low pressures, e.g., from about atmospheric to about 1000 psig and relatively low temperatures. Hydrogenation temperatures range from about 60 to 200° C. with most hydrogenations preferably being carried out at a temperature of 170° to 190° C. As with conventional nitrile hydrogenation, a solvent may be used in the process although one is not necessary. Conventional solvents include those organic solvents such as the aromatic hydrocarbons e.g. benzene, toluene, xylene, chlorinated hydrocarbons such as chlorobenzene, dichlorobenzene, bromobenzene, dibromobenzene, and aliphatic solvents such as cyclohexane, cycloheptane, tetrahydrofuran, dioxane, and so forth may be used.

Surprisingly, too, the proportion of secondary amine produced in the hydrogenation is not directly related to the proportion of individual metals, particularly the secondary metals, e.g. rhodium, ruthenium, or palladium, in the catalyst system. One might expect an "averaging" effect when incorporating such metals with cobalt or nickel. As is known cobalt and nickel tend to produce primary amines in preference to secondary and tertiary amines, while palladium tends to produce secondary and tertiary amines. Yet, a small amount of platinum 10 or the palladium component results in secondary amine concentrations that are not proportional to the concentration of these metal components in the catalyst system.

The proportion of the primary amine, or alternatively, the proportion of secondary amine, obtained during initial hydrogenation of the nitrile feed component can be enhanced by altering the process conditions. As one might expect from the prior art, conversion of the nitrile to secondary amine is enhanced through the removal of ammonia, the reduction in pressure and the elevation of reaction temperature. Whereas the hydrogenation temperature may be carried out as low as 60° C. preferably within a range of from 170° to 190° C., the temperature is raised to a temperature ranging from about 140° to 220° C and preferably from about 180° to 200° C.

The following examples are provided to illustrate various embodiments of the invention and are not intended to restrict the scope thereof.

EXAMPLE 1

Production of Butylamines

Catalyst Preparation

Several catalysts were prepared by precipitation of salt solutions onto an alumina support. Bimetallic catalysts containing more than one metal were obtained by coprecipitating solutions of metal salts onto a single alumina support. After the catalyst was prepared, the catalyst was reduced at 500° C. in the presence of hydrogen. Hydrogenation was accomplished by charging the catalyst to a ½" ID tubular reactor wherein hydrogen was passed over the catalyst at a rate of 20–30 cc/min. After 10 min. of purging the reactor, the contents were heated to 500° C. The system was held at temperature for 1 hr, cooled to room temperature, and purged with nitrogen for 30 min. The catalyst was then recovered in air at room temperature.

Hydrogenation Procedure

A 300cc autoclave reactor was used with all hydrogenations carried out at a 1500 rpm stirring rate to minimize hydrogen mass transfer as a limitation to reaction rate. The desired pre-reduced catalyst charge was weighed and added to the pressure vessel. The feed (100g) was then added to the reactor. The reactor was closed, leak tested, purged three times with nitrogen and then purged three times with hydrogen. The reactor was then pressurized with hydrogen to 500 psig and heated to the desired reaction temperature with agitation. When the reaction temperature was reached, the reactor pressure was adjusted to 500 psig. The reactor was connected through a pressure controller to a ballast tank filled with hydrogen. The volume and hydrogen pressure of the ballast tank was chosen to be sufficient to provide all of the hydrogen necessary for the reaction without dropping below 500 psig. The volume was also small enough so that the ballast pressure drop during the reaction gave an accurate measure of the hydrogen consumed. The ballast pressure was followed versus time as a measure of the rate of hydrogenation. By calculating, the ballast pressure change (known volume), the molar hydrogen consumption was determined. When the reaction test was completed, the ballast line was closed, the reactor cooled and purged with nitrogen. The reaction mixture was then removed through the charge line/filter. Catalyst life studies were done by adding the feed through the charge line/filter and repeating the procedure except for the activation of the catalyst.

Conditions and results for the hydrogenation of butyronitrile using nickel based catalysts are shown in Tables 1a and 1b.

TABLE 1a

Hydrogenation of 100 g butyronitrile at 125° C. and 500 psi pressure
using Ni/Pd catalyst at loading of 1.5 wt % of butyronitrile

| CATALYST USED | USE | $T_{95}$ (min.)[a] | CONV. (%) | SELECTIVITY (%) | | |
|---|---|---|---|---|---|---|
| | | | | $BuNH_2$[b] | $Bu_2NH$[c] | $Bu_3N$[d] |
| 20% Ni/1% Pd/$Al_2O_3$[h] | 1 | 118 | 99.7 | 67.6 | 31.9 | 0.6 |
| | 2 | 61 | 99.6 | 64.5 | 34.4 | 1.0 |
| | 3 | 60 | 99.8 | 64.4 | 34.5 | 1.1 |
| 1% Pd/$Al_2O_3$ | 1 | 480[e] | 79.8 | 0.0 | 6.1 | 93.2 |
| | 2 | 170[f] | 24.4 | 0.0 | 18.9 | 78.7 |
| 2% Pd/$Al_2O_3$ | 1 | 350[e] | 80 | 0.0 | 6.8 | 92.5 |
| | 2 | 260[e] | 43[f] | 0.0 | 9.8 | 88.7 |
| 20% Ni/2.5% Pd/$Al_2O_3$[h] | 1 | 88 | 99.9 | 68.3 | 30.8 | 1.0 |
| | 2 | 78 | 100.0 | 67.7 | 31.1 | 1.2 |
| | 3 | 75 | 99.9 | 68.6 | 30.1 | 1.4 |
| 20% Ni/0.25% Pd/$Al_2O_3$[h] | 1 | 160 | 100.0 | 69.8 | 29.6 | 0.7 |
| | 2 | 150 | 99.9 | 68.2 | 30.7 | 1.1 |
| | 3 | 160 | 100.0 | 68.3 | 30.4 | 1.3 |
| 20% Ni/$Al_2O_3$ | 1 | 240 | 99.9 | 66.0 | 32.9 | 1.1 |
| | 2 | 210 | 99.9 | 64.5 | 33.8 | 1.6 |
| | 3 | 236 | 99.8 | 53.5 | 44.2 | 2.3 |
| Raney Ni[g] | 1 | 50 | 100.0 | 81.8 | 18.2 | 0.0 |
| | 2 | 100 | 100.0 | 78.9 | 21.0 | 0.1 |
| | 3 | 90 | 99.9 | 77.9 | 21.9 | 0.2 |
| 10% Ni/2% Pd/$Al_2O_3$[h] | 1 | 105 | 100.0 | 64.7 | 34.5 | 0.8 |
| | 2 | 80 | 100.0 | 63.4 | 35.8 | 0.8 |
| | 3 | 75 | 100.0 | 63.0 | 36.1 | 0.9 |

[a] time for 95% conversion
[b] $BuNH_2$ = butylamine
[c] $Bu_2NH$ = dibutylamine
[d] $Bu_3N$ = tributylamine
[e] time for given conversion
[f] hydrogenation ceased after 170 min.
[g] Raney Ni A4000
[h] bimetallic catalyst TABLE 1b Hydrogenation of 100 g butyronitrile at 125° C. and 500 psi pressure
with a physical mixture of 20% Ni/$Al_2O_3$ and 1% Pd/$Al_2O_3$
at a catalyst loading of 3 wt % and Ni:Pd = 20:1

| CATALYST | USE | $T_{95}$ (min.)[a] | CONV. (%) | SELECTIVITY (%) | | |
|---|---|---|---|---|---|---|
| | | | | $BuNH_2$[b] | $Bu_2NH$[c] | $Bu_3N$[d] |
| 20% Ni/$Al_2O_3$ and 1% Pd/$Al_2O_3$ | 1 | 160 | 99.8 | 25.0 | 53.2 | 21.8 |
| | 2 | 170 | 100.0 | 25.9 | 58.5 | 14.7 |
| | 3 | 185 | 99.8 | 17.3 | 65.9 | 16.8 |

[a,b,c,d] Same as Table 1a

Tables 1a and 1b show hydrogenation of butyronitrile using nickel/palladium bimetallic catalysts and physical mixtures of the two catalyst components compared to the individual catalyst components themselves.

Tables 1a and 1b shows the 20%Ni/1%Pd/$Al_2O_3$ bimetallic catalyst has a very high activity compared to catalysts made with the primary metals and does not deactivate with use. The bimetallic Ni-Pd (20%Ni/1%Pd/$Al_2O_3$) catalyst completes the butyronitrile hydrogenation in 60 min. whereas the 1%Pd/$Al_2O_3$ catalyst takes 480 min. to give 80% conversion. In addition, both the 1% and 2% Pd/$Al_2O_3$ catalysts deactivate severely with use, the 1% Pd/$Al_2O_3$ giving only 24% conversion in 3 hr. by the second use. The 20% Ni/$Al_2O_3$ catalyst takes about 220 min. to complete the hydrogenation. A physical mixture of 20%Ni/$Al_2O_3$ and 1%Pd/$Al_2O_3$ when used as a catalyst for the hydrogenation of butyronitrile completed the hydrogenation in about 180 min. compared to 60 min. with the bimetallic Ni-Pd catalyst. These results show that the bimetallic Ni-Pd catalyst is much more active compared to the physically mixed Ni and Pd catalysts, but both catalyst systems are more active than the individual metals alone as catalysts. Recall that the 1% and 2% Pd/$Al_2O_3$ catalysts were extremely inactive under the reaction conditions. The effect of palladium loading on the catalyst was measured by varying the palladium loading of a 20%Nid/$Al_2O_3$ catalyst from 0.25% to 2.5%. All catalysts were subjected to three uses.! The 20%Ni/1%Pd/$Al_2O_3$ catalyst had shown the highest activity with a 60 min. hydrogenating time after 3 uses compared to 236 min. for the 20%Ni/$Al_2O_3$ catalyst after 3 uses. Increasing the palladium loading beyond 1% did not appear to increase the activity.

The 10%Ni/2%Pd/$Al_2O_3$ and 20%Ni/1%Pd/$Al_2O_3$ catalysts showed similar activity indicating that the level of nickel in the bimetallic catalyst could be as low as 10%.

Hydrogenation of butyronitrile with a Raney nickel catalyst was effected and those results also are tabulated in Table 1a. The Raney nickel catalyst had about 90% nickel and since the catalysts were tested at 1.5 wt% catalyst loading the Raney nickel catalyst has about 4.5 times more nickel than all the other catalyst tested. Therefore, the bimetallic 20%Ni/1%Pd/Al$_2$O$_3$ catalyst had similar activity to the Raney nickel catalyst at one-fourth the level of nickel allowing one to substantially reduce the amount of Ni catalyst employed in the hydrogenation process.

The product selectivities are another interesting feature of the bimetallic catalysts. Table 1a also gives the selectivity of primary and secondary amines as a function of palladium loading. The level of primary and secondary amines does not change with palladium loading. Interestingly, the product selectivity of 20%Ni/2.5%Pd/Al$_2$O$_3$ is very similar to 20%Ni/Al$_2$O$_3$ and not to 2%Pd/Al2O$_3$. The latter normally gives very high levels of tertiary amines. These results show that the interaction of nickel and palladium in the form of a bimetallic catalyst produces a product slate having the characteristics of nickel and does not produce a product slate of intermediate characteristics.

EXAMPLE 2

Hydrogenation of 100g Butyronitrile Using Ni/Rh Catalysts

The procedure of Example 1 was repeated except that a nickel/rhodium catalyst was substituted for the nickel/palladium catalyst. Comparison was made against the single rhodium catalyst alone. The results are shown in Tables 2a and 2b.

Tables 2a and 2b show that the bimetallic 20%Ni/1%Rh/Al$_2$O$_3$ catalyst is about three times as active as the 20%Ni/Al$_2$O$_3$ catalyst and about 8 times as active as the 1%Rh/Al$_2$O$_3$ catalyst. The 1%Rh/Al$_2$O$_3$ catalyst takes about 500 min. to complete the hydrogenation and the 20%Ni/Al$_2$O$_3$ catalyst takes about 230 min. to complete the hydrogenation! . The bimetallic 20%Ni/1%Rh/Al$_2$O$_3$ takes only about 70–75 min. to complete the hydrogenation. The physical mixture of 20%Ni/Al$_2$O$_3$ and 1%Rh/Al$_2$O$_3$ (Table 2b) also takes about 110 min. to complete the hydrogenation. The significant part is that the rate of hydrogenation of the nitrile is much faster whether the catalyst is in the bimetallic or physical form, than when the individual metals are employed alone. However, the bimetallic catalyst is more active than the physical mixture.

EXAMPLE 3

Hydrogenation of 100 g Butryonitrile Using Ni/Ru Catalyst

The procedure of Example 1 was repeated except that a nickel/ruthenium catalyst was substituted for the nickel/palladium catalyst. Comparison was made against the single ruthenium catalyst. The results are set forth in Table 3.

TABLE 2a

Hydrogenation of 100 g butyronitrile at 125° C. and 500 psi pressure at a catalyst loading of 1.5 wt % of butyronitrile

| CATALYST | USE | T$_{95}$ (min.)$^a$ | CONV. (%) | SELECTIVITY (%) | | |
|---|---|---|---|---|---|---|
| | | | | BuNH$_2$$^b$ | Bu$_2$NH$^c$ | Bu$_3$N$^d$ |
| 20% Ni/1% Rh/Al$_2$O$_3$$^h$ | 1 | 75 | 100.0 | 68.9 | 30.4 | 0.6 |
| | 2 | 62 | 99.8 | 66.7 | 32.4 | 0.9 |
| | 3 | 57 | 99.9 | 66.9 | 32.0 | 1.0 |
| 1% Rh/Al$_2$O$_3$ | 1 | 502$^e$ | 84.1 | 9.4 | 84.2 | 6.3 |
| | 2 | 482$^e$ | 92.2 | 10.5 | 83.2 | 6.3 |
| 20% Ni/Al$_2$O$_3$ | 1 | 240 | 99.9 | 66.0 | 32.9 | 1.1 |
| | 2 | 210 | 99.9 | 64.5 | 33.8 | 1.6 |
| | 3 | 236 | 99.8 | 53.5 | 44.2 | 2.3 |

$^{a,b,c,d,e\ and\ h}$Same as Table 1a

TABLE 2b

Hydrogenation of 100 g butyronitrile at 125° C. and 500 psi pressure
Catalyst loading of 3.0 wt % of butyronitrile
Physical mixture of 20% Ni/Al$_2$O$_3$ and 1% Pd/Al$_2$O$_3$ at a Ni:Rh = 20:1.

| CATALYST | USE | T$_{95}$ (min.)$^a$ | CONV. (%) | SELECTIVITY (%) | | |
|---|---|---|---|---|---|---|
| | | | | BuNH$_2$$^b$ | Bu$_2$NH$^c$ | Bu$_3$N$^d$ |
| 20% Ni/Al$_2$O$_3$ and 1% Rh/Al$_2$O$_3$ | 1 | 104 | 99.5 | 45.0 | 53.3 | 1.7 |
| | 2 | 108 | 99.9 | 40.7 | 57.3 | 2.0 |

$^{a,b,c,d}$Same as Table 1

TABLE 3

Hydrogenation of 100 g butyronitrile at 125° C. and 500 psi pressure
Catalyst loading 1.5 wt % of butyronitrile

| CATALYST | USE | $T_{95}$ (min.)[a] | CONV. (%) | SELECTIVITY (%) | | |
|---|---|---|---|---|---|---|
| | | | | $BuNH_2$[b] | $Bu_2NH$[c] | $Bu_3N$[d] |
| 20% Ni/1% Ru/Al$_2$O$_3$[h] | 1 | 150 | 99.9 | 68.9 | 30.5 | 0.6 |
| | 2 | 78 | 99.8 | 67.9 | 31.1 | 1.0 |
| | 3 | 73 | 99.6 | 69.1 | 30.1 | 0.8 |
| 20% Ni/Al$_2$O$_3$ | 1 | 240 | 99.9 | 66.0 | 32.9 | 1.1 |
| | 2 | 210 | 99.9 | 64.5 | 33.8 | 1.6 |
| | 3 | 236 | 99.8 | 53.5 | 44.2 | 2.3 |
| 5% Ru/Al$_2$O$_3$[e] | 1 | 320 | 100.0 | 71.0 | 28.3 | 0.1 |
| | 2 | 400 | 100.0 | 73.4 | 25.6 | 0.2 |

[a,b,c,d and h]same as Table 1a
[e]Hydrogenation was very slow at 125° C. Therefore, the hydrogenation was carried out at 150° C.

The 20%Ni/1%Ru/Al$_2$O$_3$ utilized for the hydrogenation of butyronitrile shows this bimetallic catalyst has a higher activity than either of the 20%Ni/Al2O$_3$ or the 5%Ru/Al$_2$O$_3$ catalysts. The 20%Ni/1%Ru/Al$_2$O$_3$ catalyst required only 75 min. to complete the hydrogenation while the 20% Ni/Al$_2$O$_3$ catalyst required 230 min. to complete the hydrogenation. The 5%Ru/Al$_2$O$_3$ catalyst required about 300 min. to complete the hydrogenation. These results show that the addition of ruthenium to a supported nickel catalyst makes the resultant catalyst very active for the hydrogenation of nitriles whether in bimetallic or physical form. These results also show that the bimetallic catalyst is more active than catalysts made with the primary metals.

COMPARATIVE EXAMPLE 4

Hydrogenation of 100 g Butyronitrile Using Nickel/Copper Catalyst

The procedure of Example 1 was repeated except that a new set of catalysts based on nickel/copper which had been utilized in the prior art were tested as compared to the nickel catalysts of Example 1. Table 4 sets forth the catalysts, conditions and results for the hydrogenation using 20%Ni/1%Cu/Al$_2$O$_3$ and 20% Ni/Al$_2$O$_3$ catalysts.

TABLE 4

Hydrogenation of 100 g butyronitrile at 125° C. and 500 psi pressure
Catalyst loading of 1.5 wt % of butyronitrile

| CATALYST | USE | $T_{95}$ (min.)[a] | CONV. (%) | SELECTIVITY (%) | | |
|---|---|---|---|---|---|---|
| | | | | $BuNH_2$[b] | $Bu_2NH$[c] | $Bu_3N$[d] |
| 20% Ni/1% Cu/Al$_2$O$_3$[h] | 1 | 172 | 99.8 | 58.0 | 36.5 | 5.5 |
| | 2 | 280 | 99.8 | 63.0 | 34.8 | 2.1 |
| 20% Ni/Al$_2$O$_3$ | 1 | 240 | 99.9 | 66.0 | 32.9 | 1.1 |
| | 2 | 210 | 99.9 | 64.5 | 33.8 | 1.6 |
| | 3 | 236 | 99.8 | 53.5 | 44.2 | 2.3 |

[a,b,c,d and h]are the same as Table 1

The results show that the activity of the 20%Ni/1%Cu/Al$_2$O$_3$ catalyst is quite similar to that obtained with the 20% Ni/Al$_2$O$_3$ catalyst. The Ni/1%M/Al$_2$O$_3$ (M =Rh,Ru,Pd) catalysts apparently do not undergo catalyst decay or deactivation from use to use while the 20%Ni/1%Cu/Al$_2$O$_3$ catalyst does undergo decay from use to use. Compared to the 20%Ni/1%M/Al$_2$O$_3$ ( M=Rh,Ru,Pd) catalysts, the prior art, 20%Ni/1%Cu/Al$_2$O$_3$ catalysts are only about one-third as active.

EXAMPLE 5

Hydrogenation of 100 g Butyronitrile Using Cobalt/Rhodium Catalyst

The procedure of Example 2 was repeated except that a cobalt/rhodium catalyst was used instead of a nickel/rhodium catalyst. Table 5 gives the results for the hydrogenation of butyronitrile with a 20%Co/1%Rh/Al$_2$O$_3$ catalyst and a comparison to the single catalytic component.

TABLE 5

Hydrogenation of 100 g butyronitrile at 500 psi pressure at a catalyst loading of 1.5 wt % butyronitrile

| CATALYST | USE | Temp (°C.) | $T_{95}$ (min.)[a] | CONV. (%) | SELECTIVITY (%) $BuNH_2$[b] | $Bu_2NH$[c] | $Bu_3N$[d] |
|---|---|---|---|---|---|---|---|
| 20% Co/1% Rh/Al$_2$O$_3$[h] | 1 | 125° C. | 300 | 95.3 | 54.8 | 44.7 | 0.5 |
|  | 2 | 125° C. | 163 | 100.0 | 61.5 | 38.2 | 0.3 |
|  | 3 | 125° C. | 120 | 99.9 | 59.8 | 39.7 | 0.5 |
|  | 4 | 125° C. | 120 | 98.9 | 57.6 | 41.6 | 0.8 |
| 20% Co/Al$_2$O$_3$ | 1 | 125 C. | 140 | 8 | 32.0 | 64.8 | 3.2 |
| 20% Co/Al$_2$O$_3$ | 1 | 175° C. | 305 | 100.0 | 75.0 | 24.7 | 0.2 |
|  | 2 | 175° C. | 250[e] | 78.2 | 57.6 | 42.2 | 0.2 |
|  | 3 | 175° C. | 420 | 100.0 | 72.3 | 25.7 | 0.2 |
| 1% Rh/Al$_2$O$_3$ | 1 | 125° C. | 502[e] | 84.1 | 9.4 | 84.2 | 6.3 |
|  | 2 | 125° C. | 482[e] | 92.2 | 10.5 | 83.2 | 6.2 |

[a,b,c,d]Same as Table 2.

The activity of this catalyst increased from first to second use and reached a plateau. No reason is given for the increase in activity from the initial hydrogenation. Perhaps the catalyst was not fully reduced. From the table, the Co/1%Rh/Al$_2$O$_3$ catalyst took 120 min. to complete the hydrogenation at 125° C. while the 20%Co/Al$_2$O$_3$ prior catalyst achieved only 8% conversion in 140 min. When the hydrogenation temperature was increased to 150° C., the hydrogenation rate was still low and the temperature had to be raised to 175° C. for the hydrogenation to proceed at reasonable rates. At 175° C. it took about 300 min. to complete the hydrogenation in the first use and the catalyst deactivated by the third use and took 420 min. to complete the hydrogenation. The 1%Rh/Al$_2$O$_3$ took min. to complete the first hydrogenation. These results clearly show that the hydrogenation activity of the bimetallic 20%Co/1%Rh/Al$_2$O$_3$ catalyst is higher than the catalyst made with their primary metals. The product of the hydrogenation with the Co/Rh bimetallic catalyst contained 60% primary amines to 40% secondary amines similar to 20% Co/Al$_2$O$_3$ catalyst and not the rhodium catalyst which gave secondary amines.

EXAMPLE 6

Hydrogenation of 100 g Butyronitrile Using Cobalt/Palladium Catalyst

The procedure of Example 1 was repeated except that a cobalt/palladium bimetallic catalyst was compared to the individual catalyst component. Table 6 sets forth the results.

TABLE 6

Bitmettallic Catalyst Comparison
Hydrogenation of 100 g butyronitrile at 500 psi pressure at a catalyst loading of 1.5 wt % butyronitrile

| CATALYST | USE | Temp (°C.) | $T_{95}$ (min.)[a] | CONV. (%) | SELECTIVITY (%) $BuNH_2$[b] | $Bu_2NH$[c] | $Bu_3N$[d] |
|---|---|---|---|---|---|---|---|
| 20% Co/1% Pd/Al$_2$O$_3$[h] | 1 | 125° C. | 500 | 99.9 | 63.9 | 34.3 | 1.9 |
|  | 2 | 150° C. | 92 | 99.8 | 53.0 | 44.7 | 2.2 |
|  | 3 | 150° C. | 83 | 99.2 | 54.8 | 42.8 | 2.3 |
|  | 4 | 125° C. | 200 | 100.0 | 55.0 | 41.7 | 3.0 |
| 1% Pd/Al$_2$O$_3$ | 1 | 125° C. | 480[e] | 79.8 | 0.0 | 6.1 | 93.2 |
|  | 2 | 125° C. | 170[e] | 24.4 | 0.0 | 18.9 | 78.7 |
| 20% Co/Al$_2$O$_3$ | 1 | 175° C. | 306 | 100.0 | 75.0 | 24.7 | 0.2 |
|  | 2 | 175° C. | 250[e] | 78.2 | 57.6 | 42.2 | 0.2 |
|  | 3 | 175° C. | 420 | 100.0 | 72.3 | 25.7 | 0.2 |

[a,b,c,d and h]Same as Table 1
[e]Time for given conversion.

Table 6 summarizes the results with the 20%Co/1%Pd/Al$_2$O$_3$ catalyst for the hydrogenation of butyronitrile. This Co/Pd catalyst underwent activation from first to second use and took 200 min. to complete the hydrogenation at 125° C. It took min. to complete the hydrogenation at 150° C. Secondary amine product distribution was greater with the bimetallic catalysts containing cobalt. The reaction product slate contained about 40% secondary amines and 60% primary amines, compared to a typical 20% secondary amine, 80% primary amine product slate when distribution with the Co/Al$_2$O$_3$ catalyst was used alone.

EXAMPLE 7

Hydrogenation of 100 g Butyronitrile Using Cobalt/Ruthenium Catalyst

The procedure of Example 3 was repeated except that a cobalt/ruthenium catalyst was used instead of a nickel/ruthenium catalyst. Table 7 sets forth the results.

TABLE 7

Hydrogenation of 100 g butyronitrile at 500 psi pressure
Catalyst loading of 1.5 wt % butyronitrile

| CATALYST | USE | Temp (°C.) | $T_{95}$ (min.)[a] | CONV. (%) | SELECTIVITY (%) $BuNH_2$[b] | $Bu_2NH$[c] | $Bu_3N$[d] |
|---|---|---|---|---|---|---|---|
| 20% Co/1% Ru/Al$_2$O$_3$[h] | 1 | 150° C. | 360 | 100.0 | 78.6 | 21.4 | 0.0 |
|  | 2 | 150° C. | 240 | 100.0 | 78.1 | 21.9 | 0.0 |
| 5% Ru/Al$_2$O$_3$ | 1 | 150° C. | 320 | 100.0 | 71.0 | 28.3 | 0.1 |
|  | 2 | 150° C. | 400 | 100.0 | 73.4 | 25.6 | 0.2 |
| 20% Co/Al$_2$O$_3$ | 1 | 175° C. | 306 | 100.0 | 75.0 | 24.7 | 0.2 |
|  | 2 | 175° C. | 250[e] | 78.2 | 57.6 | 42.2 | 0.2 |
|  | 3 | 175° C. | 420 | 100.0 | 72.3 | 25.7 | 0.2 |

[a,b,c,d and h]Same as Table 1
[e]Time for given conversion.

The 20%Co/1%Ru/Al$_2$O$_3$ had the lowest activity of all the bimetallic catalysts tested (compare Tables 1–7 for results). The Co/Ru catalyst took 290 min. to complete the hydrogenation at 150° C. and the product distribution of the hydrogenated product was similar to typical Co/Al$_2$O$_3$ catalysts.

In summary, the results show that the addition of from about 0.05–10% of a second metal selected from Rh, Ru or Pd to a supported nickel catalyst makes the catalyst very active for the hydrogenation of nitriles. The addition of rhodium or palladium to a cobalt containing catalyst also enhances catalyst activity. The addition of ruthenium to the cobalt also enhances the activity of the cobalt although not to the extent that the other metal enhance activity.

Although not intending to be bound by theory, it is believed the high activity and selectivity of the catalyst can be explained as follows: In view of the fact that the loading of the second metal to nickel or cobalt is relatively low, the synergistic effect may occur via one of two mechanisms. According to the first, nickel hydrogenates intermediates that inhibit the hydrogenation by the second metal.. According to a second mechanism, the second metal (Rh, Ru, or Pd) makes the nickel component of the catalyst (1–60%) more active. Evidence for such a mechanism comes from the observed effect on the reduction temperature of these catalyst. The 20%Ni/Al$_2$O$_3$ catalyst can be reduced at about 400° C. The 20%Ni/1%Pd/Al$_2$O$_3$ catalyst can be reduced at a temperature about 70° C. lower than the 20%Ni/Al$_2$O$_3$ catalyst. The reason for the lower reduction temperature for both the bimetallic catalyst and the physical mixture of the catalyst is believed caused by a hydrogen spillover mechanism. With the bimetallic catalysts, activated hydrogen on the noble metal can spill over to nickel for subsequent hydrogenation. Since the hydrogenation reactions are carried out typically at 125° C. to 175° C., the noble metal can continuously supply activated hydrogen to the nickel surface so that it is active for the hydrogenation of nitriles.

What is claimed is:

1. In a process for the catalytic hydrogenation of an aliphatic or an aromatic nitrile wherein a feedstock containing said nitrile is contacted with hydrogen in the presence of a hydrogenation catalyst, the improvement which comprises: utilizing a bimetallic hydrogenation catalyst comprising nickel in combination with rhodium or ruthenium or cobalt in combination with palladium, rhodium, or ruthenium wherein said bimetallic hydrogenation catalyst is carried on a single support.

2. The process of claim 1 wherein the nitrile is an aliphatic mononitrile having from 2–10 carbon atoms.

3. The process of claim 2 wherein the bimetallic hydrogenation catalyst comprises from about 1–60% by weight nickel or cobalt and from about 0.01 to 10% by weight of rhodium, ruthenium, or palladium based upon the total weight of the catalyst.

4. The process of claim 3 wherein the bimetallic hydrogenation catalyst consists essentially of nickel in combination with rhodium or ruthenium.

5. The process of claim 4 wherein said nickel is present in an amount from about 10 to 25% by weight and the rhodium or ruthenium is present in an amount from about 0.5 to 2.5% each based upon the weight of the catalyst.

6. The process of claim 5 wherein said support is alumina.

7. The process of claim 6 wherein said nitrile is selected from the group consisting of acetonitrile, propionitrile, butyronitrile, valeronitrile and glutaronitrile.

8. The process of claim 7 wherein the bimetallic hydrogenation catalyst consists essentially of nickel and rhodium.

9. The process of claim 3 wherein the bimetallic hydrogenation catalyst consists essentially of cobalt in combination with rhodium, ruthenium or palladium.

10. The process of claim 9 wherein said cobalt is present in an amount from about 5 to 25% and the rhodium, ruthenium or palladium is present in an amount from about 0.5 to 2.5%.

11. The process of claim 10 wherein said support is alumina.

12. The process of claim 11 wherein said nitrile is selected from the group consisting of acetonitrile, propionitrile, butyronitrile, valeronitrile and glutaronitrile.

13. The process of claim 12 wherein the bimetallic hydrogenation catalyst consists essentially of cobalt and palladium or cobalt and rhodium.

14. The process of claim 13 wherein the nitrile is butyronitrile.

* * * * *